United States Patent [19]

Kirkland et al.

[11] 4,160,728

[45] Jul. 10, 1979

[54] BIMODAL CHROMATOGRAPHIC RESOLVING ZONE

[75] Inventors: Joseph J. Kirkland, Wilmington; Wallace W. Yau, Newark, both of Del.

[73] Assignee: E. I. Du Pont de Nemours and Company, Wilmington, Del.

[21] Appl. No.: 826,171

[22] Filed: Aug. 22, 1977

Related U.S. Application Data

[63] Continuation-in-part of Ser. No. 748,769, Dec. 8, 1976, abandoned.

[51] Int. Cl.$^2$ .............................................. B01D 15/08
[52] U.S. Cl. ................................... 210/31 C; 55/67; 55/386; 106/286.8; 252/449; 252/477 R; 210/198 C
[58] Field of Search .............. 210/31 C, 198 C; 55/67, 55/386; 106/288 B, 286; 252/449, 477 R, 313 S, 317

[56] References Cited

U.S. PATENT DOCUMENTS

| | | | |
|---|---|---|---|
| 3,488,922 | 1/1970 | Kirkland | 55/67 |
| 3,505,785 | 4/1970 | Kirkland | 55/67 |
| 3,757,490 | 9/1973 | Ma | 55/67 |
| 3,782,075 | 1/1974 | Kirkland | 210/198 C |

OTHER PUBLICATIONS

Multiple Columns in Chromatography by Baker and Zinn in Control Engineering, Jan. 1961, pp. 77–81.
Selection of GPC Columns by Calculations to Produce a Column Set with Desired Molecular Weight Range and Calibration Range by Saunders and Rehfeldt in Journal of Chromatography Science. Oct., 1973, pp. 511–513.
"Linearity of Calibration Curves in Gel Permeation Chromatography and Mixed Gel Columns" by Ishida et al. in Kobunshi Kagaku (Chem. High Polymers) 27, 297, 33–39 (1970) translation.

*Primary Examiner*—John Adee

[57] ABSTRACT

Disclosed herein is a resolving zone for a chromatograph comprising a plurality of porous, silica macroparticles chosen to provide the resolving zone with a bimodal pore distribution, the average pore size for each mode being such that the linear portions of the molecular weight calibration curve for each pore size in the bimodal distribution are nonoverlapping and the pore volume of each mode being such that the aforesaid linear portions are substantially parallel. The macroparticles can be either totally or superficially porous. The resolving zone can be composed of either a plurality of macroparticles each having a bimodal pore distribution or a plurality of macroparticles having one pore size distribution and a plurality of macroparticles having another pore distribution.

40 Claims, 10 Drawing Figures

4,160,728

BIMODAL CHROMATOGRAPHIC RESOLVING ZONE

CROSS-REFERENCE TO RELATED APPLICATION

This application is a continuation-in-part of copending application U.S. Ser. No. 748,769 filed Dec. 8, 1976 now abandoned.

BACKGROUND OF THE INVENTION

1. Field of the Invention

This invention relates to chromatography, particularly size exclusion chromatography, and to the composition of the resolving zones used in such chromatography. It also relates to a process for performing chromatographic separation.

2. Discussion of the Prior Art

U.S. Pat. No. 3,505,785 discloses superficially porous microspheriods, having an average diameter in the range of 5 to 500 microns, which are composed of an impervious core coated with a multiplicity of monolayers of colloidal inorganic particles having an average size in the range of 0.005 to 1.0 microns. U.S. Pat. No. 3,855,172 discloses microspheriods which are porous throughout and have an average diameter in the range of 0.5 to 20 microns. They are composed of colloidal inorganic refractory particles having an average diameter in the range of 0.005 to 1.0 microns.

The use of such microspheriods in chromatography, particularly size-exclusion chromatography is well-known. In such application, porous microspheroids are used as packings for the chromatograph resolving zone and functions to separate the components of a sample based on differences in hydrodynamic size of the components. The molecular weight (MW) of the components can be calculated as a function of the hydrodynamic size. A plot of the molecular weight fraction eluted at a given retention volume ($V_R$) for a particular packing material reveals that for a given pore volume in the packing material, certain molecular weight fractions are totally excluded because of their large size and certain molecular weight fractions are totally permeating because of their small size. Between these two extremes is a range of molecular weight fractions that will be preferentially retarded by contact with the porous particles, and materials containing these molecular weight fractions can be fractionated by that particular packing material.

The actual working relationship in size exclusion chromatography is the molecular weight calibration curve which is normally a logarithmic plot of the molecular weight versus the retention volume. Molecular weight calibration curves characteristically have a substantially linear portion so that the molecular weight of a retained fraction of a sample can be determined accurately if the retention volume for that particular molecular weight fraction occurs in the linear portion of the molecular weight calibration curve and less accurately if it occurs outside that linear range. Molecular weight calibration curves characteristically have linear portions that span approximately two decades in the log molecular weight scale for a single pore size. To obtain a calibration curve with a linear portion spanning more than two decades of the molecular weight scale, the tendency is to use a chromatographic resolving zone composed of many columns, each having different pore sizes. Specifically, as taught by "Know More About Your Polymer", a 1976 publication of Waters Associates, Milford, Mass., to expand the linear range of the molecular weight calibration curve so that materials containing a wide range of molecular weight fractions can be separated and detected, four or five columns are combined, each with molecular weight calibration curves whose linear portions overlap one another.

Unfortunately, the range of expected linear molecular weight calibration does not occur. The linear portion of the molecular weight calibration curve for the combined particles can be increased in this way but the maximum appears to be only about three decades, which often is less than the range of molecular weight found in normal sample compositions.

SUMMARY OF THE INVENTION

According to this invention, there is provided a resolving zone for a chromatograph which provides a wider range of linearity in its molecular weight calibration curve and avoids the inconvenience of using multiple columns with overlapping linear calibration. This resolving zone comprises a plurality of porous macroparticles chosen to provide the resolving zone with a bimodal pore distribution, the average pore size for each mode being such that the linear portion of the molecular weight calibration curves for each pore size in the bimodal distribution are substantially nonoverlapping, the pore volume of each mode being such that the aforesaid linear portions are substantially parallel. As used herein, the term "average pore size" means volume average pore size. To achieve the maximum range of the linear portion of the molecular weight calibration curve, the pore sizes of the modes of the bimodal distribution should be about one order of magnitude apart. The term "bimodal pore distribution" as used herein is not meant to exclude the use of more than two modes of particle size distribution so long as two adjacent modes have substantially parallel linear non-overlapping portions of their calibration curves, the average pore volume of each of the two adjacent modes being separated about one order of magnitude.

The macroparticles useful in this invention can be refractory particles such as silica or alumina or they can be non-refractory such as crosslinked polymer gels. In the preferred embodiment the macroparticles are refractory macroparticles composed primarily of silica and the component of the bimodal pore distribution having the smaller average pore size provides about 30 to about 60%, preferably about 40 to about 60%, more preferably about 40 to 55% and still more preferably, about 45 to 55%, of the total pore volume of the macroparticles in the resolving zone with the balance of the total pore volume being provided by the component of the bimodal distribution having the larger average pore size. The resolving zone can be composed of a plurality of macroparticles, each having a bimodal pore distribution, or it can be composed of a plurality of macroparticles each having one pore distribution combined with a plurality of macroparticles having another pore distribution.

This invention also provides an improved process for performing chromatographic separation comprising the steps of:
 (a) placing the material to be separated in a carrier fluid;
 (b) contacting the carrier fluid with a resolving zone comprising a plurality of porous, refractory, macroparticles chosen to provide the resolving zone with a bimodal pore distribution the average pore size for each mode being such that the linear portions of the molecular weight calibration curve for each pore size in the bimodal distribution are nonoverlapping, and the pore volume of each mode being such that the aforesaid linear portions are substantially parallel, and (c) determining the extent of retention of the materials by the resolving zone.

BRIEF DESCRIPTION OF THE DRAWINGS

The present invention can best be described by reference to the following figures in which.

DETAILED DESCRIPTION OF THE INVENTION

Figure 3:
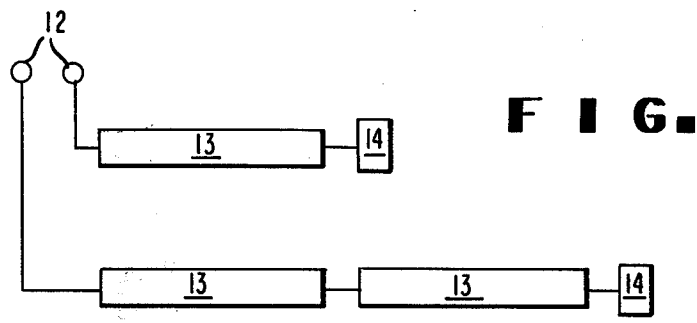
FIG. 3 is a schematic representation of a liquid chromatograph showing the carrier fluid injection point 12, resolving zone 13 and detector 14; showing particularly resolving zones composed of 1 and 2 separate columns.

In size exclusion chromatography, a chromatograph such as that shown schematically in FIG. 3 is used. A material to be separated is injected into a carrier fluid stream at some injection point 12 and forced under pressure through a chromatographic resolving zone 13 to a detector 14. In passing through the resolving zone, the materials in the carrier fluid contact the packing material in the resolving zone and are retained for a time characteristic of their molecular weight (MW). In time, as more volume of carrier fluid passes through the chromatographic column, the material temporarily retained by the packing material is eluted from the column. The detector determines when each component of the material leaves the resolving zone. The output of the detector is characteristically a peak such as that shown schematically in the bottom of FIG. 4.

The resolving zones used in size exclusion chromatography are generally columns packed with porous particles such as those described in U.S. Pat. No. 3,505,785 and U.S. Pat. No. 3,855,172, or more recently the macroporous microspheroids disclosed in U.S. Pat. No. 4,040,286 by R. K. Iler and J. J. Kirkland.

Figure 1:
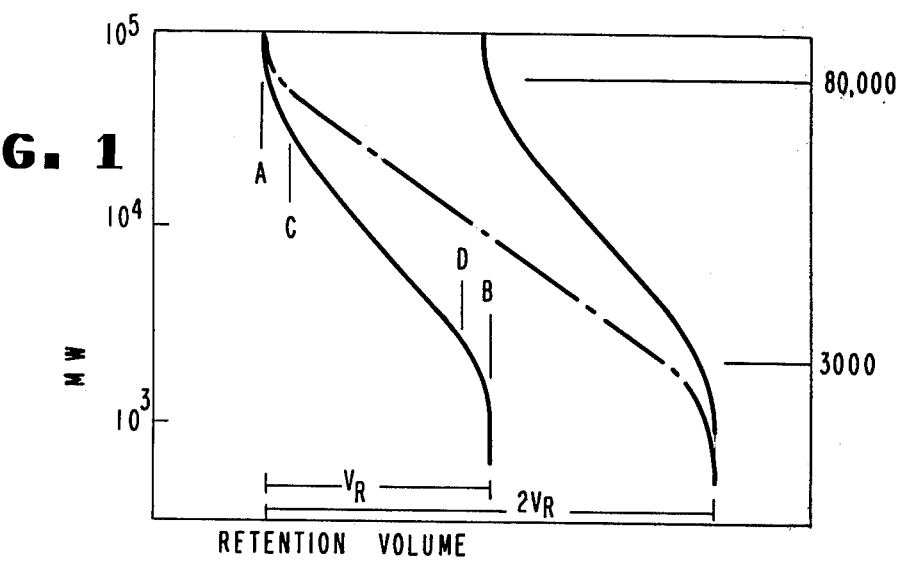
FIG. 1 is a representative calibration curve of molecular weight plotted on a log scale against retention volume.

Using such packing materials, a typical relationship of the log MW (a function of solute hydrodynamic radius) versus retention volume ($V_R$) is shown by the single solid line on the left-hand side of FIG. 1. The limiting retention volume at a point A is known as the total exclusion volume, which is determined by the maximum pore size available for permeation by the solute materials that are totally rejected from the internal porosity elute at this retention volume, and solutes corresponding to this molecular weight and larger are not fractionated by the system. Point B represents the volume associated with species which totally permeate the internal pores of the packing material, and is known as the total permeation volume. Thus, materials corresponding to this MW and smaller cannot be substantially fractionated by this separating system. The difference between retention volumes A and B represents partial permeation of solutes, and it is within this volume range that separation occurs. The difference between the retention volume at B and retention volume at A is a function of the total internal pore volume of the packing. Between retention volumes at A and B there is an approximately linear region of the log MW versus retention volume curve (points C to D) which is described by the following equations:

$$V_R = C_1 - C_2 \log MW \tag{1}$$

and $$MW = D_1 e^{-D_2 V_R} \tag{2}$$

$C_2$ is the slope of the linear portion of the calibration curve (in ml/decade-MW) and $C_1$ is the intercept of this linear portion. To extract molecular weight information from this calibration plot, experimental chromatograms and equation 2 above are utilized. $D_1$ relates to the intercept of this linear portion of the calibration curve and $D_2$ relates to its slope. These equations are well-known to those skilled in the art and are widely used by those characterizing macromolecules.

The additive characteristics of two identical columns used in size-exclusion chromatography is well known. As indicated in FIG. 1, connecting two identical columns (same particles, same length) with identical calibration curves indicated by the two solid lines is equivalent to doubling the length of a single column. As indicated, connecting these two columns increases the total available pore volume, thus increasing the retention volume range between total permeation and total exclusion, but maintaining the same molecular weight fraction range. As shown in FIG. 1 when two columns are connected, the molecular weight fraction range remains about 3,000 to 80,000, even though the retention volume is doubled. The calibration curve for the combination of the two columns is shown by the dashed line. The additive function describing this relationship is:

$$C_2 = \sum_i (C_2)_i, \text{ or} \tag{3}$$

$$D_2 = 1/\sum_i (1/D_2)_i \tag{4}$$

Figure 2:
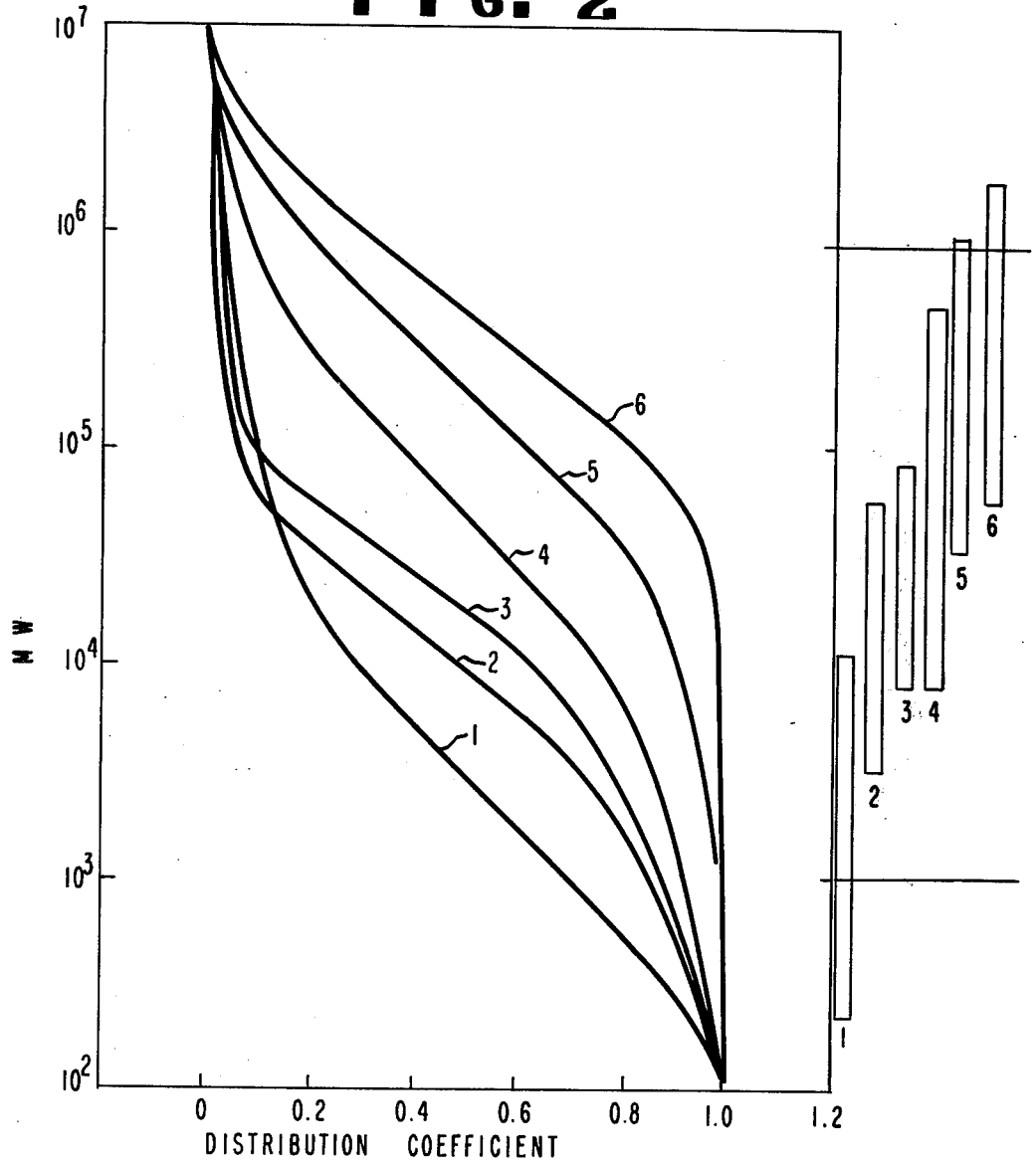
FIG. 2 is a calibration curve for resolving zone composed of six different particles having differing pore sizes.

Traditionally, polymer fractionation has been accomplished with packings having the broadest possible pore-size distribution. This is normally obtained by connecting several columns of different pore size to produce a separating system covering the molecular weight range of interest. FIG. 2 shows a series of molecular weight calibration curves for six different chromatographic resolving zone, each filled with porous silica particles having different pore sizes. The designation and average pore volume for these six particles is given in Table I below:

TABLE I

| | Designation | Pore Size (A°) |
|---|---|---|
| 1 | PMS-50 | 60 |
| 2 | PMS-300 | 125 |
| 3 | PMS-600 | 195 |
| 4 | PMS-800 | 300 |
| 5 | PMS-1500 | 750 |
| 6 | PMS-4000 | 3500 |

These particles were made as described in U.S. Patent Application Ser. No. 639,111, filed June 15, 1976 and U.S. Pat. No. 3,782,075.

The bar graphs to the right of FIG. 2 indicate the linear range of each calibration plot. To achieve a linear combined calibration curve spanning a molecular weight range from $10^3$ to $10^6$, a combination of six columns traditionally would be used, each composed of the individual particles corresponding to the six graphs.

In this invention the relationship given in equation 3 has been exploited to improve the accuracy, versatility, and convenience of the size-exclusion process. This relationship predicts a previously unrecognized phenomena, namely, that to obtain a wide linear log MW-retention volume relationship, a series of columns having substantially overlapping linear molecular weight fractionation ranges (i.e., linear portions) should not be used. Rather, columns having only two pore sizes, chosen so that the linear portions of the molecular weight versus retention volume curves do not overlap, should be used. This produces a far wider linear range in the calibration curve. As shown representatively in FIG. 4, a polymodal pore distribution in the resolving zone produces a narrow linear portion on the molecular weight calibration curve, and a bimodal distribution produces a much wider linear portion. The calibration curve for the polymodal distribution does not encompass the entire molecular weight distribution of the sample within its linear range, whereas the calibration curve for the bimodal distribution does.

Figure 4:
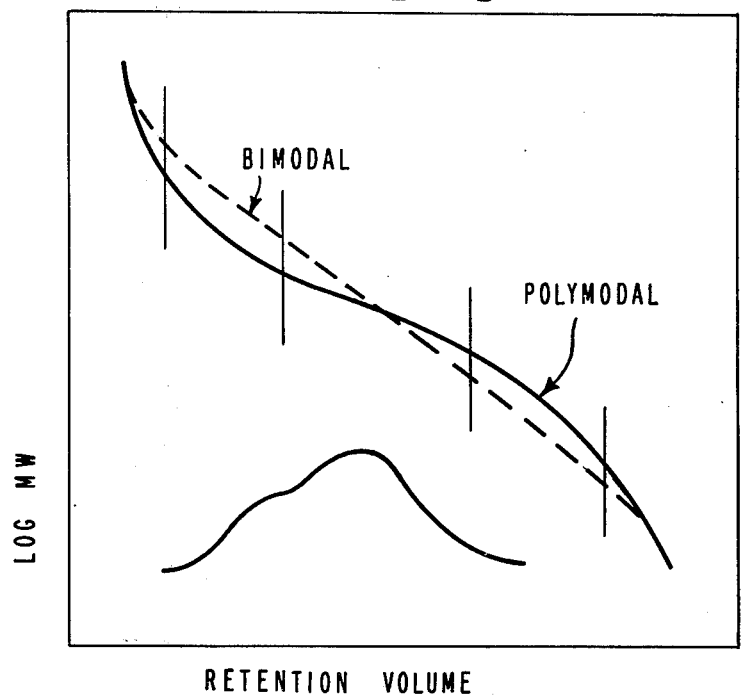
FIG. 4 is a representative calibration curve for a bimodal and a polymodal resolving zone.

The advantage of using chromatographic columns having a bimodal pore distribution, whether connecting columns of individual pore size or using columns containing a physical mixture of particles that are two pore sizes can, therefore, be seen from FIG. 4. Molecular weight calibration curves of the type shown by the bimodal pore size distribution is greatly preferred when attempting to characterize a polymer with the type of molecular weight distribution illustrated at the bottom of the plot.

Figure 9:
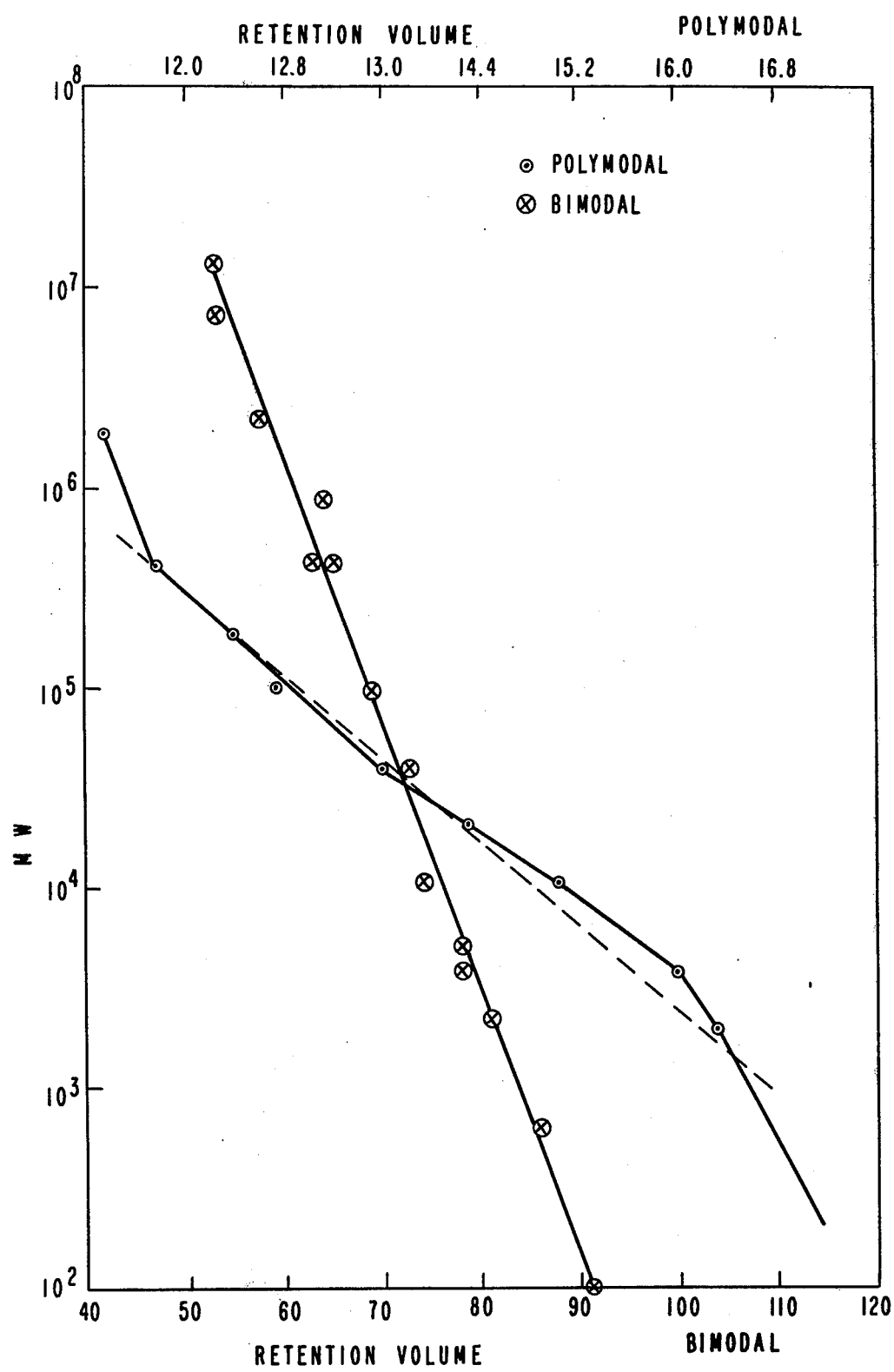
FIG. 9 is a comparison of a calibration curve obtained using two of the particles, which had nonoverlapping particle size distributions, shown in FIG. 2 compared with a calibration curve obtained using five of the particles all having overlapping particle size distributions shown in FIG. 2.

A quantitative comparison of a polymodal pore-size distribution versus bimodal pore-distribution system is given in FIG. 9. FIG. 9 shows a polystyrene calibration curve for a polymodal and for a bimodal resolving zone. The set of columns used to produce the polymodal distribution are filled with a packing material labeled 1, 2, 4, 5 and 6 in FIG. 2. The individual columns have substantially overlapping calibration plots as in the traditional mode. The approximate linear calibration range (dashed line is the linear fit) of this combined broad pore-size distribution set is only about two and one-half decades of molecular weight. On the other hand, the bimodal distribution shown in FIG. 9, obtained by connecting columns of only two pore sizes (that of particles 1 and 5 in FIG. 2) results in a linear molecular weight calibration curve spanning more than four decades of molecular weight.

Figure 10:
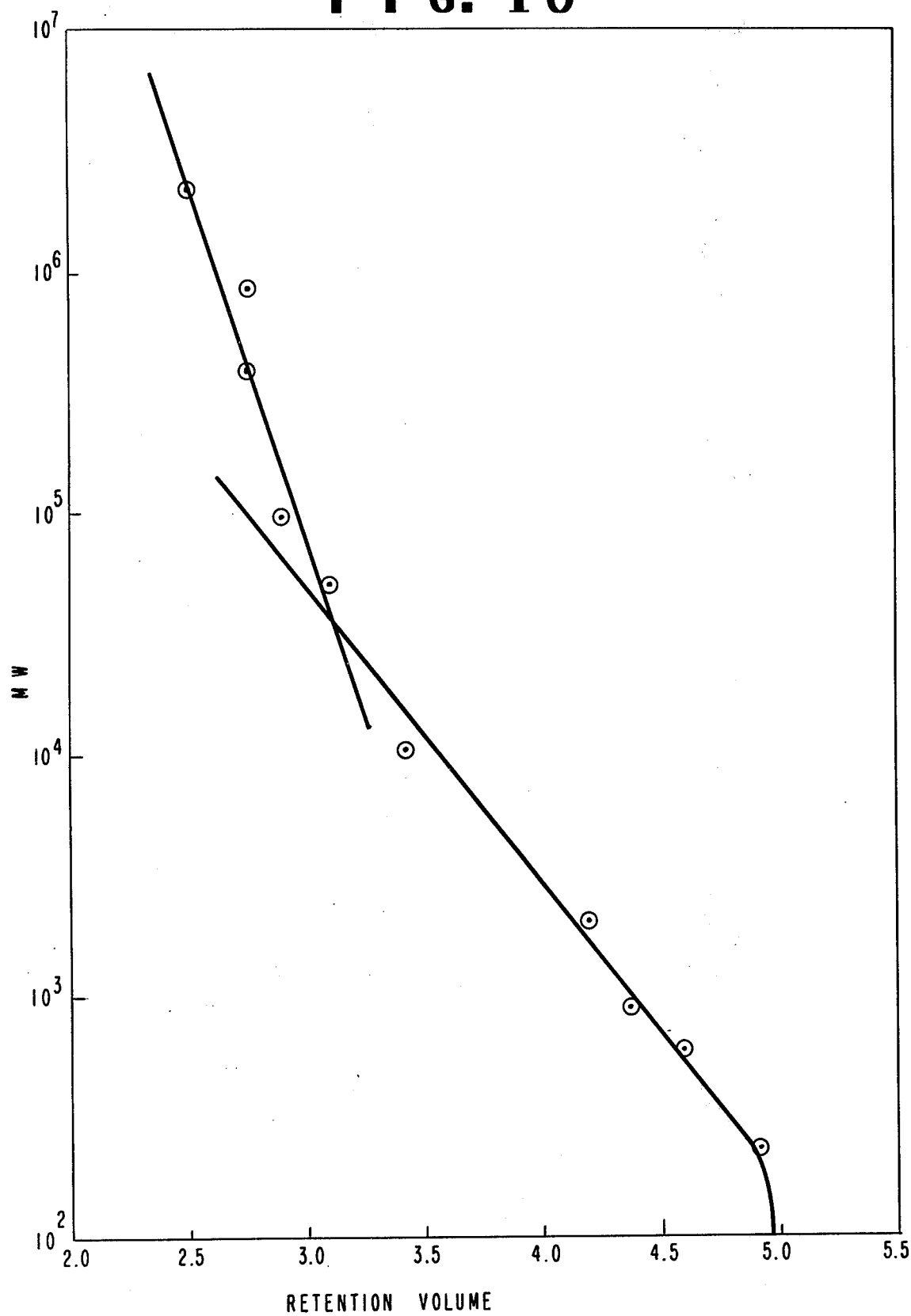
FIG. 10 is a calibration curve obtained using the bimodal particles such as that shown in FIG. 6.

To obtain these unexpected and improved results, the individual calibration curves for the two pore sizes used in the bimodal distribution must not overlap. This is achieved by choosing particles with the appropriate pore size. The average pore sizes of the bimodal distribution should be about one order of magnitude apart. With this bimodal approach, linear calibration curves having up to five decades of molecular weight range are obtained. A trimodal arrangement of similar type could result in up to seven decades molecular weight range linearity. In addition to having molecular weight calibration curves which are non-overlapping, the internal pore volume of the two modes should be such that the linear portions of the calibration curves are substantially parallel. The term substantially parallel means that the shapes of the linear portions of the calibration curves need not be exactly parallel provided some deviation from linearity can be accepted. For example, reference to FIG. 9 indicates that the overlapping polymodal calibration curve which represents the prior art is far from linear over the range predicted. When about 30 to 60%, preferably 40 to about 60%, more preferably about 40 to 55% and still more preferably about 45 to 55%, of the total pore volume of the macroparticles in each resolving zone is provided by the component of the bimodal pore distribution having the lower average pore size with the balance provided by the component having the larger average pore size, the linear portions of the individual calibration curves are substantially parallel. Reference to FIG. 10 shows the deviation from linearity in the calibration curve when the pore volume ratio is 40:60. In the most preferred embodiment, however, each component of the bimodal pore distribution should provide about 50% of the total pore volume of the macroparticle in the resolving zone to reduce deviation from linearity in the calibration curve.

Best results are obtained using packing materials with a very narrow pore-size distribution. Pore size distributions of each of the bimodal systems should be 1.0 or less ($2\delta$) as shown in conventional log-normal plots of mercury porosimetry measurements. Ranges of 0.5 ($2\delta$) are preferred. Within these ranges, pore size distribution is an insignificant factor in determining the $D_2$ of the calibration plot, and the internal volume of the particles is dominant in determining the $D_2$ of the calibration plot. If the pore size distribution is larger than the values given above, then the interrelationship of both pore size distribution plus internal volume determines the slope of the calibration curve.

The bimodal pore distribution used in the present invention can be achieved in one of two ways. The bimodal pore distribution can be provided by a plurality of microparticles each having a bimodal pore distribution. In this instance, a single column such as that shown in the upper portion of FIG. 3 can be used. Alternately the bimodal pore distribution can be provided by using a plurality of macroparticles having one pore distribution and a plurality of macroparticles having another pore distribution. While particles with different pore size distributions can be mixed into one column, the packing of such columns is less convenient and it is best to use two or more columns, each packed with a single type particle.

Figure 5:
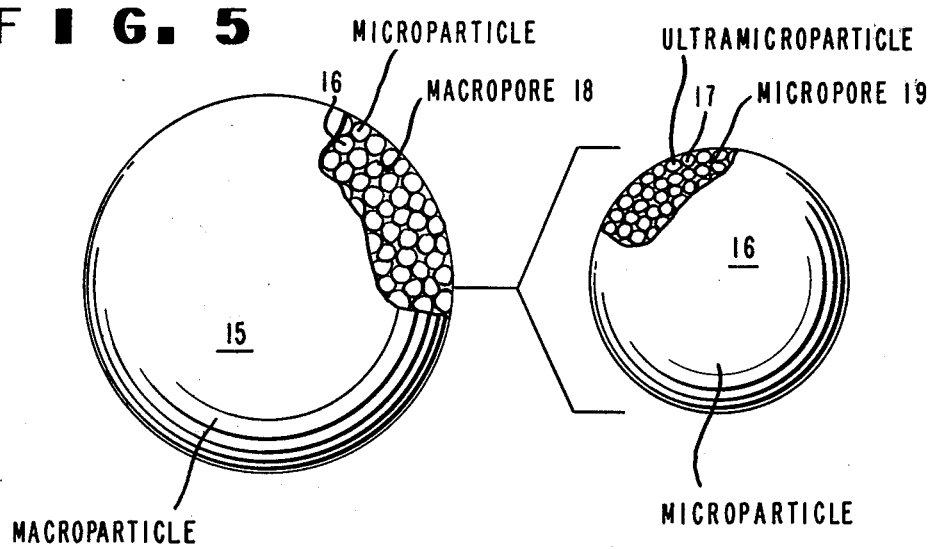
FIG. 5 is a partially cut-away schematic representation of one embodiment of a totally porous macroparticle having a bimodal pore distribution.

Individual particles of the desired pore size to produce the bimodal pore distribution can be produced by the techniques described in the patents and the patent applications mentioned above. The disclosure in these patents and applications is hereby incorporated by reference into the present specification. Polymeric gels, alumina and the wide range of refractory particles mentioned in these documents can be used, but silica is the preferred material, particularly for chromatographic separations. Particles having a bimodal pore distribution can either be totally porous or superficially porous macroparticles. The term macroparticle, as used herein, means the composite macroparticle (either totally or superficially porous) having an average diameter in the range of about 0.5 to about 500 microns. The totally porous embodiment of this particle is shown in FIG. 5. Here the macroparticle 15 has an average diameter of about 0.5 to 500 microns. Preferred macroparticles having average diameters of about 5 to 50 microns. The macroparticle is composed of a plurality of microparticles 16, each having an average diameter in the range of about 0.005 to about 1.0, preferably about 0.005 to 0.5, microns. The individual microparticles are in turn composed of a plurality of ultramicroparticles 17 having an average diameter in the range of about 1.0 to about 30.0 nanometers with 2-20 being preferred. Between each microparticle is a macropore 18, and between each ultramicroparticle is a micropore 19. While these particles can in general have any shape, it is preferred that they have a spherical shape so that the macroparticles are actually macrospheres, the microparticles are microspheres and the ultramicroparticles are ultramicrospheres. The spherical nature of these materials improves their performance in chromatographic columns.

Figure 6:
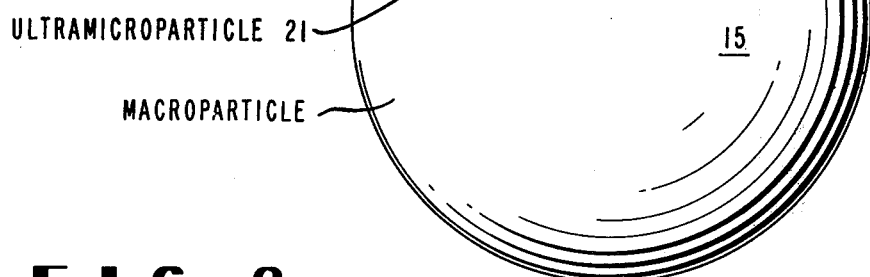
FIG. 6 is a partially cut-away schematic representation of a second embodiment of a totally porous macroparticle with a bimodal pore distribution.

Alternatively, as shown in FIG. 6, the totally porous macroparticle 15 can be composed of a core 20 comprising a plurality of ultramicroparticle 21 having an average diameter in the range of about 1 to about 30 nanometers, and a skin composed of a multiplicity of microparticles 22, each having a diameter in the range of about 0.1 to about 1.0 microns, or more commonly, 0.1 to 0.5 microns. The totally porous macroparticle produced by currently known techniques preferably have a diameter in the range of about 0.5 to about 50 microns.

Figure 7:
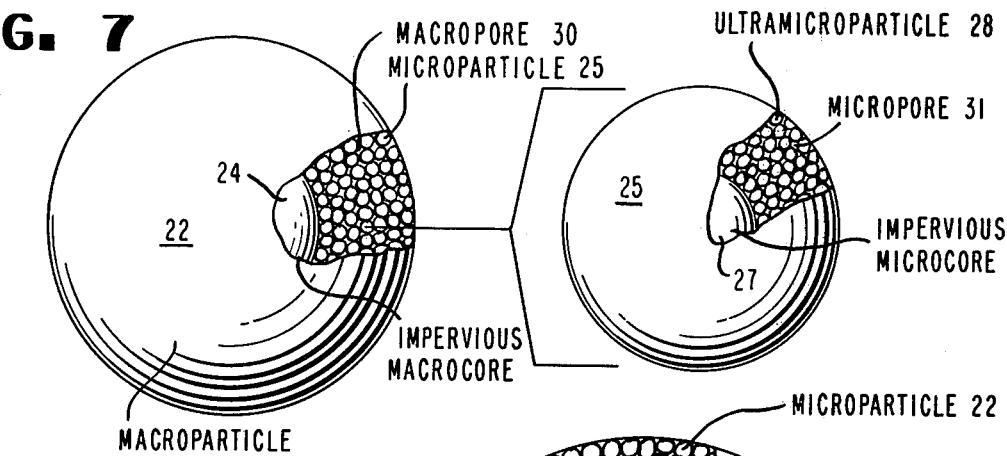
FIG. 7 is a partially cut-away schematic representation of an embodiment of a superficially porous macroparticle having a bimodal pore distribution.

One embodiment of a superficially porous macroparticle is shown in FIG. 7. Such macroparticle 22 has a diameter in the range of about 0.5 to about 500 or preferably, 5 to 50, microns and comprise an impervious macrocore 24 and a coating of a multiplicity of like monolayers of like colloidal inorganic microparticles 25 joined to and surrounding the core. Each microparticle has an average diameter in the range of about 0.005 to about 1.0 microns or preferably, 0.1 to 0.5 microns and comprises from about 0.2 to about 25% of the total volume of the macroparticle. The microparticle can be similar to that shown in FIG. 5, composed totally of ultramicroparticle, or it can be similar to the microparticle shown in FIG. 7, composed of an impervious microcore 27 and a coating of a multiplicity of like monolayers of like colloidal inorganic ultramicroparticles 28 joined to and surrounding the core.

In either case, for the totally porous or the superficially porous particles, the pores between the individual microparticles in the macroparticle shall be referred to as the macropore 30 and provides one mode of the bimodal pore distribution, and the pores between the individual ultramicroparticle shall be referred to as the micropore 31 and provides the other mode of the bimodal pore distribution. Recent terminology sometimes defines pores of the size designated as "micropores" herein as "mesopores".

EXAMPLE I

The following describes the preparation of pellicular particles with a bimodal pore-size distribution. Such a structure is shown in FIG. 7.

75 g of Zipax ® (Du Pont trademark for chromatographic support) controlled porosity support (E. I. du Pont de Nemours and Co.) (<37 μm) was stirred gently with 800 ml of 0.5% Lakeseal laboratory cleaner solution for 30 minutes. The excess solution was removed by decantation and washed with distilled water. This operation was repeated seven times, and the resulting powder filtered on a coarse sintered-glass filter and dried in air. The dry powder was then placed in a three-inch diameter coarse sintered-glass funnel and treated with 100 ml of 0.5% Zelex ® DX (Du Pont trademark for antistatic agents and mold release agents) (E. I. du Pont de Nemours and Co.) solution for five minutes with stirring. The treated beads were filtered, then washed twice with 200 ml of distilled water and dried in the funnel with vacuum.

The beads then were treated with 100 ml of 10% silica sol made from Ludox ® AS (Du Pont trademark for colloidal silica) (~140 Å silica particles supplied by E. I. du Pont de Nemours and Co.) (125 g of 30% by weight silica in Ludox ® AS diluted to 400 g with distilled water). The mixture of beads and silica sol was allowed to stand for 15 minutes in the funnel with frequent gentle stirring. Excess Ludox ® was then filtered off and the resulting wet cake washed four times by gently slurrying with about 400 ml of tap water and filtering. The cake was then allowed to air-dry in the filter under vacuum. This material was then dried at 150° C. for one hour in a circulating air oven and a small sample removed for surface area measurement.

The Zelec ® DX silica sol treatment described above was repeated three more times to build up a crust of the 140 Å silica sol ultramicroparticles on the surface of the 2000 Å silica microparticles which originally made up the crust of the Zipax ® particles. The final particles were dried, and heated at 650° C. for two hours to burn out the organic interlayer and sinter the particles into a mechanically stable condition. This sintered sample was then allowed to stand for two hours in a large excess of 0.001 M ammonium hydroxide with frequent stirring. The particles were then washed twice with a large excess of distilled water by decantation, filtered on coarse sintered-glass funnel, air-dried, and heated at 150° C. for two hours in a circulating air bath. The final material was dry-sieved with stainless screens to obtain a <38 μm fraction of 45 g.

Surface areas on the products obtained during the synthetic steps were obtained by the nitrogen flow method with the following results:

| Sample | Surface Area, $m^2/g$ |
| --- | --- |
| Starting Zipax ® | 0.89, 0.99 |
| First treatment with Ludox ® AS | 2.03, 2.09 |
| Second treatment with Ludox ® AS | 2.35, 2.46 |
| Third treatment with Ludox ® AS | 3.07, 3.01 |

-continued

| Sample | Surface Area, m²/g |
| --- | --- |
| Fourth treatment with Ludox® AS | 3.38, 3.50 |
| Sintered at 650° C. for two hours | 2.67, 2.67 |
| Final rehydrated material | 2.85, 2.86 |

A mercury porosimetry measurement of this sample showed three breaks in the mercury intrusion plot, one at about 10 microns, representing the intrusion of mercury between the individual particles, a break at about $0.07\mu$ (700 Å) representing the macropores between the sol microparticles in the crust of the initial Zipax® structure, and a break at about $0.006\mu$ (60 Å) representing the pores between the 140 Å sol ultramicroparticles which are multilayered onto the original Zipax® structure by the procedure herein described. The volumes associated with the bimodal pore-size distribution were:

Macropores—(700 Å pores)—0.011 cc/g
Micropores—(60 Å pores)—0.014 cc/g.

These data show that the final particles contained the desired bimodal pore configuration, with pores approximately one decade in size difference, and approximately equal pore volumes for each pore size.

EXAMPLE II

Particles of the type illustrated in FIG. 6 can be prepared as follows: 15 g of porous silica microspheres (PSM-40; 47 angstrom pores) made according to U.S. Pat. No. 3,782,075, Jan. 1, 1974, Joseph J. Kirkland, assigned to Du Pont; U.S. Pat. No. 3,855,172, Dec. 17, 1974, Ralph K. Iler and Herbert J. McQueston, assigned to E. I. du Pont de Nemours and Co., was treated with 200 ml of 0.001 M ammonium hydroxide, allowed to stand for 10 minutes with occasional stirring and centrifuged in a 250 ml polyethylene bottle for two minutes (from the start) at approximately 2,000 revolutions/min. The clear supernatant was decanted, and to the wet cake was added 100 ml of 0.5% Zelec® DX (E. I. du Pont de Nemours and Co.) solution which had been adjusted to pH 7 with ammonium hydroxide. The sytem was carefully slurried, then left to stand for 10 minutes with occasional gentle stirring. The resulting mixture was centrifuged for one minute using the approach described above, and the excess Zelec® DX solution decanted. The wet cake was washed twice with 200 ml of distilled water (adjusted to pH 7 with ammonium hydroxide) by carefully slurrying, centrifuging for one minute, and decanting.

To these treated particles was added 50 ml of 5% (by weight) 2000 Å silica sol mixture adjusted to pH 8 [sol can be prepared by procedures in: W. Stober, A. Fink and E. Bohn, J. Colloid, Inter. Sci., 26, 62 (1968)], and the mixture was thoroughly slurried and occasionally stirred for 10 minutes. This mixture was centrifuged as above, decanted and excess sol retained. The coated beads were then washed twice with 200 ml of distilled water (pH 7) by slurrying, centrifuging and decanting. The second wash decantant from this process was clear. The wet cake was then filtered on a 3 $\mu$m "Nuclepore" filter and dried in a circulating air oven at 150° C. for two hours. The sample was then fired at 700° C. for one hour in a muffle furnace. A small portion of this material was subjected to scanning electron micron analysis which showed an excellent coverage of the surface of the original beads with the 2000 Å silica sol. No bare spots were seen on the particles.

A second layer of 2000 Å silica sol was placed on the PSM particles using the technique described above, after first hydrolyzing the fired silica particles in 0.01 M hydrochloric acid overnight and eliminating the acid by washing with distilled water. The material was again treated with Zelec® DX, followed by 2000 Å sol (25 ml of "virgin" plus the recovered sol excess from the first treatment), in the manner described above. Inspection of this material by scanning electron microscopy showed the second coating was layered as desired. Very few spots were seen on the beads, and only a very small amount of particle bridging was noted.

A third, fourth, fifth, and sixth treatment of the beads were carried out in essentially the same manner as described above to build up the desired crust of 2000 Å silica sol particles on the particles. These treated beads were fired at 750° C. for one hour and rehydrolyzed by dilute acid treatment as above. SEM inspection of the final beads showed good coverage, but it was not possible to observe the exact thickness of the desired superficially porous crust.

Figure 8:
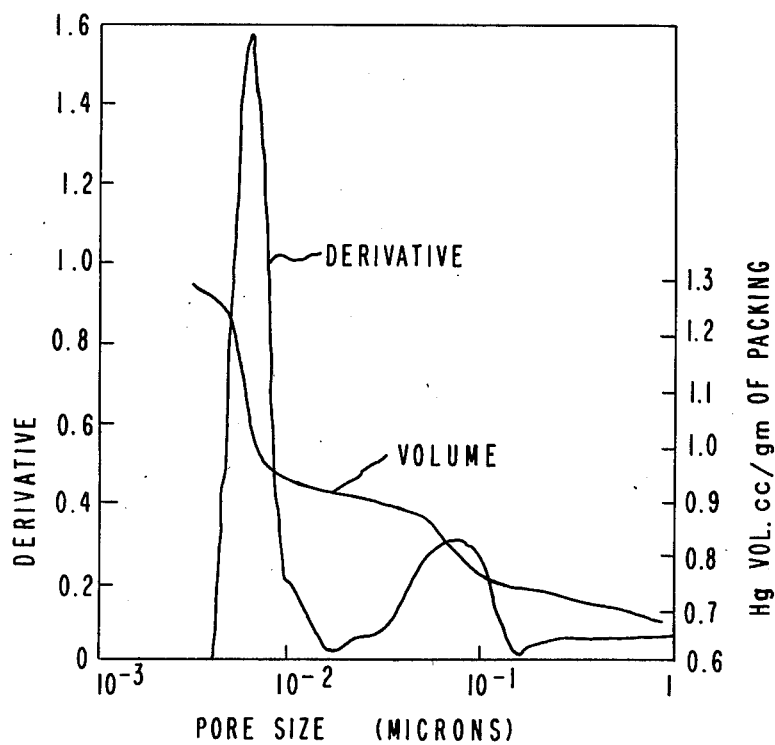
FIG. 8 is a mercury intrusion plot for particles such as that shown in FIG. 6.

Mercury intrusion measurements plotted in FIG. 8 show that the pore volume of the larger pores of these particles is about 40% of the total pore volume and the pore volume of the smaller pore volume is about 60% of the total. The log molecular weight versus retention volume calibration plot for a $25 \times 0.62$ cm i.d. column of these particles is shown in FIG. 10. Because of the difference in internal volumes associated with the two modes, there is some deviation from linearity.

We claim:

1. A resolving zone for a chromatograph comprising a plurality of macroparticles, said macroparticles being chosen to provide said resolving zone with a bimodal pore size distribution, the average pore size for each mode being such that the linear portions of the molecular weight calibration curve for each pore size in the bimodal distribution are substantially nonoverlapping and the pore volume of each mode being such that said linear portions are substantially parallel, wherein the component of the bimodal pore size distribution having a smaller average pore size provides from about 30 to 60% of the total pore volume and the component of the bimodal pore size distribution having a larger average pore size provides from about 70 to 40% of the total pore volume of the macroparticles in the resolving zone.

2. The resolving zone of claim 1 wherein each component of the bimodal pore size distribution provides about 40 to 60% of the total pore volume of the macroparticles in the resolving zone and wherein the average pore sizes of the components of the bimodal pore size distribution are about one order of magnitude apart.

3. The resolving zone of claim 2 wherein the component of the bimodal pore size distribution having the smaller average pore size provides about 40 to 55% of the total pore volume and the component of the bimodal pore size distribution having the larger average pore size provides about 45 to 60% of the total pore volume of the macroparticles in the resolving zone.

4. The resolving zone of claim 3 wherein each component of the bimodal pore size distribution provides about 45–55% of the total pore volume of the macroparticles in the resolving zone.

5. The resolving zone of claim 3 wherein the macroparticles have an average diameter of about 0.5 to 500 microns and are composed of a plurality of microparticles having a diameter of about 0.005 to about 1.0 micron and wherein each macroparticle has a bimodal pore size distribution.

6. The resolving zone of claim 3 wherein the macroparticles have an average diameter of about 0.5 to 500 microns and are composed of a plurality of microparticles having a diameter of about 0.005 to about 1.0 micron, the bimodal pore size distribution in the zone being provided by a plurality of macroparticles having an average pore size within one mode of the bimodal distribution and a plurality of macroparticles having an average pore size within the other mode of the bimodal distribution.

7. The resolving zone of claim 5 wherein said macroparticles are totally porous macroparticles having an average diameter of about 0.5 to 50 microns and are composed of a plurality of microparticles having an average diameter of 0.005 to 0.5 micron.

8. The resolving zone of claim 7 wherein the macroparticles are silica.

9. The resolving zone of claim 5 wherein the macroparticles are superficially porous having an average diameter of about 5 to 50 microns and are composed of a macrocore surrounded by microparticles having a diameter of 0.1 to 0.5 micron.

10. The resolving zone of claim 9 wherein the macroparticles are composed primarily of silica.

11. The resolving zone of claim 6 wherein the macroparticles are totally porous macroparticles having an average diameter of about 0.5 to 50 microns and are composed of a plurality of microparticles having an average diameter of about 0.005 to 0.5 micron.

12. The resolving zone of claim 11 wherein the macroparticles are silica.

13. The resolving zone of claim 6 wherein the macroparticles are superficially porous having an average diameter of about 5 to 50 microns and are composed of a macrocore surrounded by microparticles having a diameter of about 0.1 to 0.5 micron.

14. The resolving zone of claim 13 wherein the macroparticles are composed primarily of silica.

15. In a process for chromatographic separation comprising the steps
   (a) placing the material to be separated in a carrier fluid;
   (b) contacting the carrier fluid with a resolving zone; and
   (c) determining the extent of retention of said material in the zone,
the improvement comprising using a resolving zone comprising a plurality of macroparticles, said macroparticles being chosen to provide said resolving zone with a bimodal pore size distribution, the average pore size for each mode being such that the linear portions of the molecular weight calibration curve for each pore size in the bimodal distribution are substantially nonoverlapping and the pore volume of each mode being such that said linear portions are substantially parallel.

16. The process of claim 15 wherein the component of the bimodal pore size distribution having a smaller average pore size provides from about 30 to 60% of the total pore volume and the component of the bimodal pore size distribution having a larger average pore size provides from about 70 to 40% of the total pore volume of the macroparticles in the resolving zone.

17. The process of claim 16 wherein each component of the bimodal pore size distribution provides about 40 to 60% of the total pore volume of the macroparticles in the resolving zone and wherein the average pore sizes of the components of the bimodal pore distribution are about one order of magnitude apart.

18. The process of claim 17 wherein the component of the bimodal pore size distribution having the smaller average pore size provides about 40 to 55% of the total pore volume and the component of the bimodal pore size distribution having the larger average pore size provides about 45 to 60% of the total pore volume of the macroparticles in the resolving zone.

19. The process of claim 18 wherein each component of the bimodal pore size distribution provides about 45-55% of the total pore volume of the macroparticles in the resolving zone.

20. The process of claim 18 wherein the macroparticles have an average diameter of about 0.5 to 500 microns and are composed of a plurality of microparticles having a diameter of about 0.005 to about 1.0 micron and wherein each macroparticle has a bimodal pore size distribution.

21. The process of claim 18 wherein the macroparticles have an average diameter of about 0.5 to 500 microns and are composed of a plurality of microparticles having a diameter of about 0.005 to about 1.0 micron, the bimodal pore size distribution in the zone being provided by a plurality of macroparticles having an average pore size within one mode of the bimodal distribution and a plurality of macroparticles having an average pore size within the other mode of the bimodal distribution.

22. The process of claim 20 wherein said macroparticles are totally porous macroparticles having an average diameter of about 0.5 to 50 microns and are composed of a plurality of macroparticles having an average diameter of 0.005 to 0.5 micron.

23. The process of claim 20 wherein the macroparticles are superficially porous having an average diameter of about 5 to 50 microns and are composed of a macrocore surrounded by microparticles having a diameter of 0.1 to 0.5 micron.

24. The process of claim 21 wherein the macroparticles are totally porous macroparticles having an average diameter of about 0.5 to 50 microns and are composed of a plurality of microparticles having an average diameter of about 0.005 to 0.5 micron.

25. The process of claim 21 wherein the macroparticles are superficially porous having an average diameter of about 5 to 50 microns and are composed of a macrocore surrounded by microparticles having a diameter of about 0.1 to 0.5 micron.

26. A powder for chromatographic separations consisting essentially of a plurality of discrete porous macroparticles, each macroparticle having an average diameter of about 0.5 to about 500 microns and a bimodal pore size distribution, the average pore sizes of the components of the bimodal distribution being about one order of magnitude apart and the component of the bimodal distribution having the smaller average pore size provides from about 30 to 60% of the total pore volume and the component of the bimodal distribution having the larger average pore size provides from about 70 to 40% of the total pore volume.

27. The powder of claim 26 wherein the component of the bimodal pore size distribution having the smaller average pore size provides about 40 to 55% of the total pore volume and the component of the bimodal pore size distribution having the larger average pore size provides from about 60 to 45% of the total pore volume.

28. The powder of claim 27 wherein each component of the bimodal pore size distribution provides from about 45 to about 55% of the total pore volume.

29. The powder of claim 26 wherein said macroparticles are superficially porous macroparticles having an impervious core and a coating of a multiplicity of like monolayers of colloidal microparticles joined to and surrounding the core, the microparticles having a diameter of about 0.005 to about 1.0 micron and comprising from about 0.2 to about 25% of the total volume of the macroparticle.

30. The powder of claim 29 wherein the microparticles have a diameter of about 0.1 to 0.5 micron and the macroparticles have a diameter of 5 to 50 microns.

31. The powder of claim 30 wherein the macroparticles are composed principally of silica and wherein the component of the bimodal pore size distribution having the smaller average pore size provides about 40 to about 55% of the total pore volume and the component of the bimodal pore size distribution having the larger average pore size provides about 60 to 45% of the total pore volume.

32. The powder of claim 31 wherein each component of the bimodal pore size distribution provides about 45 to 55% of the total pore volume.

33. A powder of claim 26 wherein said macroparticles are totally porous, each being composed of a plurality of microparticles, the microparticles having a diameter of about 0.005 to 1.0 micron.

34. A powder of claim 32 wherein the macroparticles have a diameter of from about 5 to 50 microns and the microparticles have a diameter of 0.005 to 0.5 micron.

35. The powder of claim 34 wherein the macroparticles are composed principally of silica and wherein the component of the bimodal pore size distribution having the smaller average pore size provides about 40 to about 55% of the total pore volume and the component of the bimodal pore size distribution having the larger average pore size provides about 60 to 45% of the total pore volume.

36. The powder of claim 35 wherein each component of the bimodal pore size distribution provides about 45 to 55% of the total pore volume.

37. The powder of claim 26 wherein the macroparticles are totally porous having a core of a plurality of ultramicroparticles about 1 to 30 nanometers in diameter and a skin of a plurality of microparticles about 0.1 to 1.0 micron in diameter.

38. The powder of claim 37 wherein the macroparticles are 5 to 50 microns in diameter and the microparticles are 0.1 to 0.5 micron in diameter.

39. The powder of claim 38 wherein the macroparticles are silica and wherein the component of the bimodal distribution having the smaller average pore size provides about 40 to 55% of the total pore volume and the component of the bimodal distribution having the larger pore size provides about 60 to 45% of the total pore volume.

40. The powder of claim 39 wherein each component of the bimodal pore size distribution provides about 45 to 55% of the total pore volume.

* * * * *